(12) United States Patent
Allen (10) Patent No.: US 11,766,074 B1
(45) Date of Patent: Sep. 26, 2023

(54) THERAPEUTIC SOCK (71) Applicant: Nina Louise Allen, Decatur, GA (US)

(72) Inventor: Nina Louise Allen, Decatur, GA (US)

(*) Notice: Subject to any disclaimer, the term of this patent is extended or adjusted under 35 U.S.C. 154(b) by 0 days.

(21) Appl. No.: 17/831,895

(22) Filed: Jun. 3, 2022

(51) Int. Cl.
*A41B 11/12* (2006.01)
*D04B 1/26* (2006.01)
*A61M 35/00* (2006.01)
*A41B 11/00* (2006.01)

(52) U.S. Cl.
CPC .......... *A41B 11/003* (2013.01); *A41B 11/121* (2013.01); *A61M 35/00* (2013.01); *A61M 35/10* (2019.05); *D04B 1/265* (2013.01)

(58) Field of Classification Search
CPC ...... A61M 35/00; A61M 35/10; A61M 35/30; D04B 1/265; A41B 11/003; A41B 11/121
See application file for complete search history.

(56) References Cited

U.S. PATENT DOCUMENTS

| | | | |
|---|---|---|---|
| 3,128,763 A | 4/1964 | Langenfeld et al. | |
| 3,871,030 A * | 3/1975 | Green | A63B 47/001 2/250 |
| 3,882,868 A * | 5/1975 | Tundermann | A61F 13/068 604/293 |
| 4,351,068 A * | 9/1982 | Taylor | A41B 11/14 2/409 |
| 6,334,222 B1 | 1/2002 | Sun | |
| 7,213,420 B2 | 5/2007 | Lynch et al. | |
| 9,027,166 B1 | 5/2015 | Hagberg | |
| 9,241,513 B2 | 1/2016 | Yuen et al. | |
| 2001/0048936 A1 * | 12/2001 | Prenovitz | A61K 9/70 424/443 |
| 2003/0056276 A1 * | 3/2003 | Zimmerman | A61M 35/10 2/159 |
| 2004/0161452 A1 | 8/2004 | Petit | |
| 2004/0215120 A1 | 10/2004 | Jensen et al. | |
| 2006/0253961 A1 * | 11/2006 | Chan | A61M 35/10 2/239 |
| 2007/0074426 A1 * | 4/2007 | Dorsey | A43B 19/00 36/94 |
| 2008/0156503 A1 | 7/2008 | McSherry | |
| 2009/0172867 A1 | 7/2009 | Kopp et al. | |
| 2010/0031532 A1 | 2/2010 | Bass | |
| 2012/0180195 A1 * | 7/2012 | Shull | D04B 1/26 2/239 |
| 2013/0131572 A1 | 5/2013 | Cros et al. | |

(Continued)

FOREIGN PATENT DOCUMENTS

| CN | 201839807 U | 5/2011 |
|---|---|---|
| CN | 201894189 U | 7/2011 |

(Continued)

*Primary Examiner* — Susan S Su (57) ABSTRACT

Disclosed embodiments may include a therapeutic sock for aiding in the treatment of toe and foot ailments. The therapeutic sock may include a sock body, which may be a stocking made from nylon or a similar elastic material, with an upper section and a lower section. The lower section may include a toe end and an absorbent pad. The absorbent pad may be gauze and may contain medicine. The absorbent pad may be attached to the sock body by sewing. The upper section may include a restricting band at the leg end. The restricting band may be made of nylon or elastic and be attached to the sock body by sewing.

13 Claims, 4 Drawing Sheets

(56) References Cited

U.S. PATENT DOCUMENTS

| | | | |
|---|---|---|---|
| 2013/0178779 A1* | 7/2013 | Duda | A61F 13/06 28/167 |
| 2014/0052080 A1 | 2/2014 | Gibson et al. | |
| 2014/0088523 A1* | 3/2014 | Ottuso | A41B 11/02 604/293 |
| 2015/0257453 A1 | 9/2015 | Olsen | |
| 2019/0167462 A1* | 6/2019 | Shaffer | A61F 5/0127 |

FOREIGN PATENT DOCUMENTS

| | | |
|---|---|---|
| CN | 103750949 A | 4/2014 |
| CN | 206043461 U | 3/2017 |
| CN | 206284407 U | 6/2017 |
| CN | 207912067 U | 9/2018 |
| CN | 213281509 U | 5/2021 |
| DE | 102016112126 A1 | 1/2018 |
| EP | 1246591 A1 | 10/2002 |
| JP | 3063812 U | 11/1999 |
| JP | 2001271205 A | 10/2001 |
| KR | 200909021 U | 9/2009 |
| KR | 101266547 B1 | 5/2013 |

\* cited by examiner

THERAPEUTIC SOCK

The disclosed technology relates to a therapeutic sock or stocking and methods of manufacture thereof. Specifically, this disclosed technology relates to a sock or stocking that can hold medicine in a certain location near a person's toes or the bottom of the foot near the toes. The disclosed technology may also be used to aid in foot care treatment after injury or surgery.

BACKGROUND

Foot ailments have long been a plague on human society. Despite many advances in medicine, significant numbers of people each year are afflicted with infections and ailments in the toes and toenails such as athlete's foot or nail fungus (onychomycosis), which can be notoriously hard to treat and cure. While medical professionals can prescribe medications and a number of over-the-counter options are available to treat such ailments, keeping medicines applied to the correct area on the toes in ways that is helpful can be inherently difficult for several reasons. First, the toes are frequently moved when walking. Second, toes and feet frequently sweat, which provide good growing conditions for the assortment of infections while also washing away the medicine.

Traditional systems and methods for keeping medicine on the toes typically involve applying the medicine to the affected area and securing an adhesive bandage (e.g., a Band-Aid®) to prevent the medicine from moving. This is problematic for several reasons. First, the shape of toes makes it inherently difficult to secure an adhesive bandage. Second, the frequent sweating of the feet prevent the adhesive bandages from having good adhesion. Third, the adhesive bandage may prevent airflow from reaching the affected area, which can stifle improvement. Fourth, the adhesive on the bandage may further irritate the skin if it sticks to the infected area.

Accordingly, there is a need for improved technologies to retain medicine on the tops of toes to treat infections and other ailments. Embodiments of the present disclosure are directed to this and other considerations.

SUMMARY

Disclosed embodiments may include a therapeutic sock. The sock may include an upper section configured to extend up a leg of a user. The upper section may include a restricting band that restricts a first width of the upper section to hold the therapeutic sock in place. The sock may also include a lower section which surrounds the toes of the user. The lower section may include a front portion, a first side, a second side opposite the first side, a second width extending from the first side to the second side that is greater than the first width, and a first length extending from the front portion to the upper section. Finally, the sock may include a gauze pad attached to the front portion of the lower section along the second width.

Disclosed embodiments may include a therapeutic stocking. The stocking may include an upper section that extends up a leg of a user. The upper section may include a restricting band, which restricts a first width of the upper section to hold the therapeutic stocking in place. The stocking may also include a lower section that is made to surround toes of the user. The lower section may include a front portion, a first side, a second side opposite the first side, a second width extending from the first side to the second side that is greater than the first width, and a first length extending from the front portion to the upper section. Finally, the stocking may include an absorbent pad attached to the front portion of the lower section along the second width.

Disclosed embodiments may include a sock. The sock may include an upper section that extends around an ankle of a user. The upper section may include a restricting band. The sock may also include a lower section configured to surround toes of the user. The lower section may have a front portion, a first side, a second side opposite the first side, a width extending from the first side to the second side. Finally, the sock may have an absorbent pad attached to the front portion of the lower section along the width.

Further implementations, features, and aspects of the disclosed technology, and the advantages offered thereby, are described in greater detail hereinafter, and can be understood with reference to the following detailed description, accompanying drawings, and claims.

BRIEF DESCRIPTION OF THE DRAWINGS

Reference will now be made to the accompanying drawings, which are not necessarily drawn to scale, and which illustrate various implementations, aspects, and principles of the disclosed technology. In the drawings.

DETAILED DESCRIPTION

Some implementations of the disclosed technology will be described more fully with reference to the accompanying drawings. This disclosed technology may, however, be embodied in many different forms and should not be construed as limited to the implementations set forth herein. The components described hereinafter as making up various elements of the disclosed technology are intended to be illustrative and not restrictive. Many suitable components that would perform the same or similar functions as components described herein are intended to be embraced within the scope of the disclosed electronic devices and methods.

Reference will now be made in detail to example embodiments of the disclosed technology that are illustrated in the accompanying drawings and disclosed herein. Wherever convenient, the same reference numbers will be used throughout the drawings to refer to the same or like parts.

Figure 1:
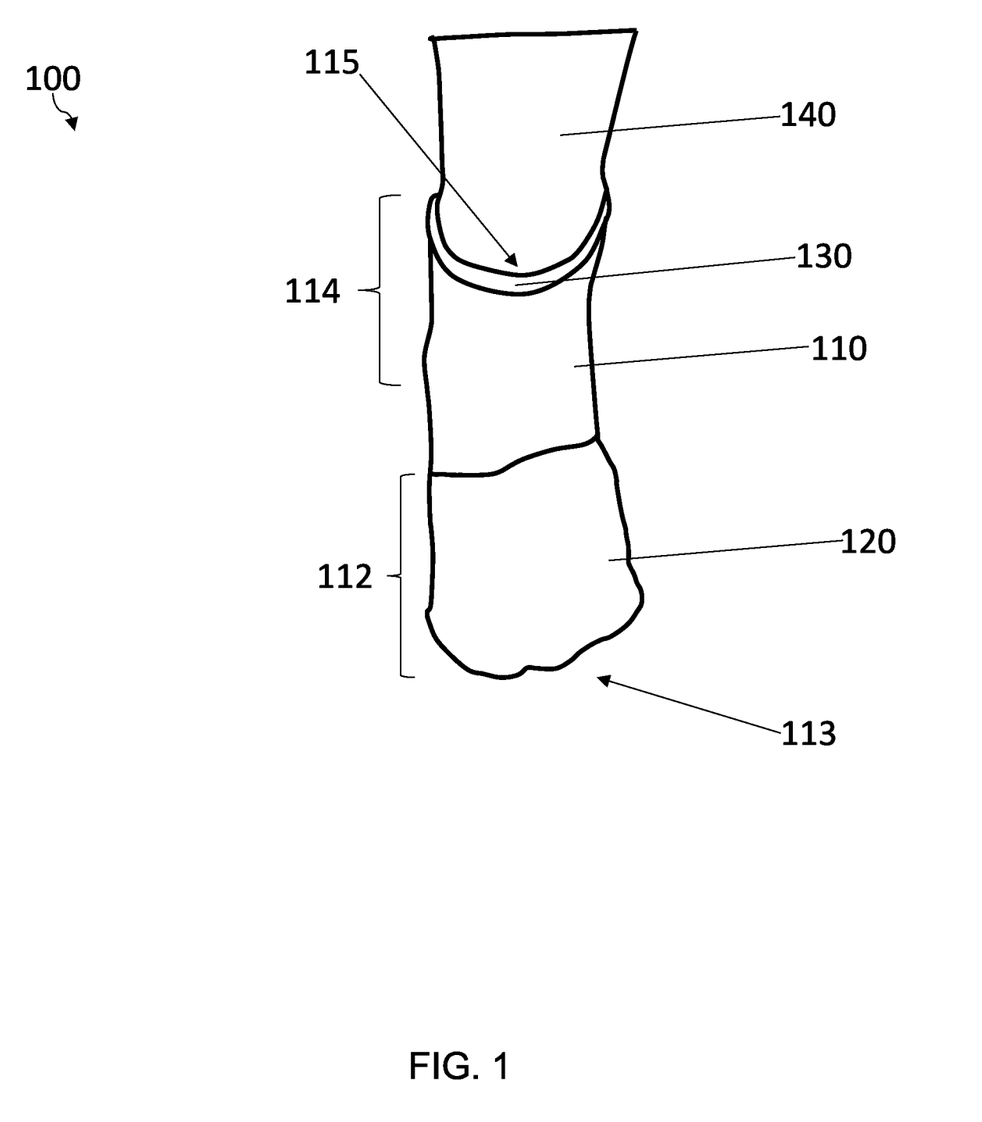
FIG. 1 is front perspective view of a therapeutic sock on a foot in accordance with certain embodiments of the disclosed technology.
Figure 2:
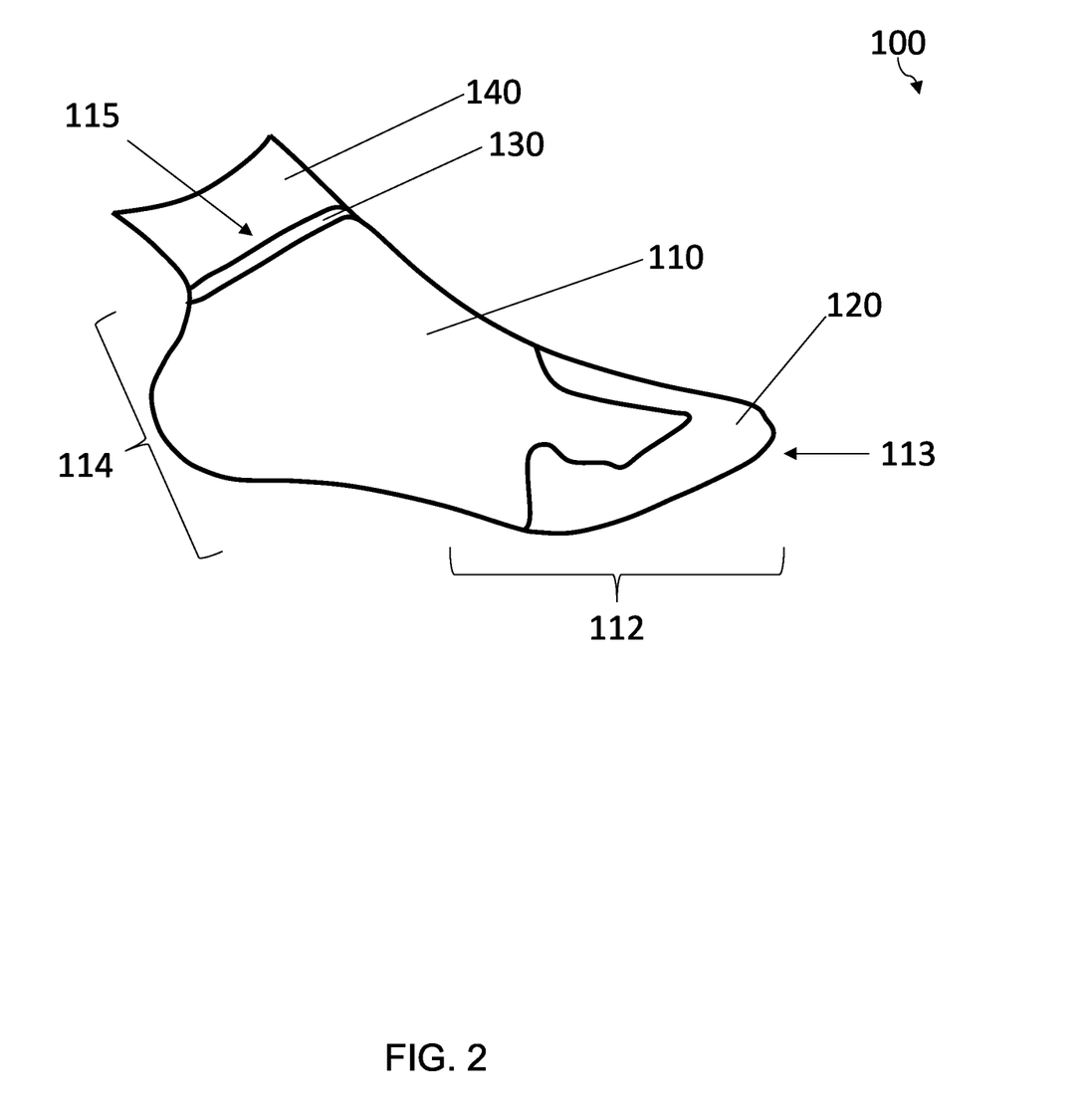
FIG. 2 is a right-side view of an example therapeutic sock on a foot according to an example implementation of the disclosed technology.

FIGS. 1 and 2 illustrate an exemplary therapeutic sock 100 in accordance with some embodiments of the disclosed technology. The therapeutic sock 100 may be used to aid in the recovery of infections of the foot or toes. The therapeutic sock 100 may be specifically used to aid in the healing of the area in between the toes or the toenails. Furthermore, the therapeutic sock 100 can aid in the care of foot sores, ulcers, or injury to the sole or ball of the foot. Additionally, the therapeutic sock 100 can aid in the recovery of foot surgery. Therapeutic sock 100 may be comprised of a sock body 110. The sock body 110 may be a stocking. Sock body 110 may be a variety of different sizes to fit different users. Alternatively, sock body 110 may be of a "one-size-fits-all" design. Sock body 110 may have a lower section 112 for wrapping around the user's toes and the lower part of the foot. The lower section 112 may contain the toe end 113 of the sock, which may completely enclose the user's toes. The lower section 112 of sock body 110 may have an absorbent pad 120 which is attached to the sock body 110 at the toe end 113 of the sock and extends rearward. The absorbent pad 120 may rest on the top of the user's toes, below the user's toes, or both while contained within the sock body 110. Sock body 110 may have an upper section 114 consisting of a portion that wraps around the user's ankle. The upper section 114 may contain ankle end 115, that has an opening for the user's leg 140 to stick out from sock body 110. The upper section 114 may contain a restricting band 130 to prevent the sock body 110 from sliding down the user's leg 140 and around the user's ankle.

The therapeutic sock 100 may be disposable and designed for a single use. Alternatively, the therapeutic sock 100 may be reusable. The therapeutic sock 100 may be washable. The therapeutic sock 100 may allow for the user to replace the absorbent pad 120 inside the sock after use. For this, the toe end 113 may have an attachment mechanism (e.g., clips) that allow the absorbent pad to be detached from the toe end of the sock and replaced with a new absorbent pad.

Figure 3:
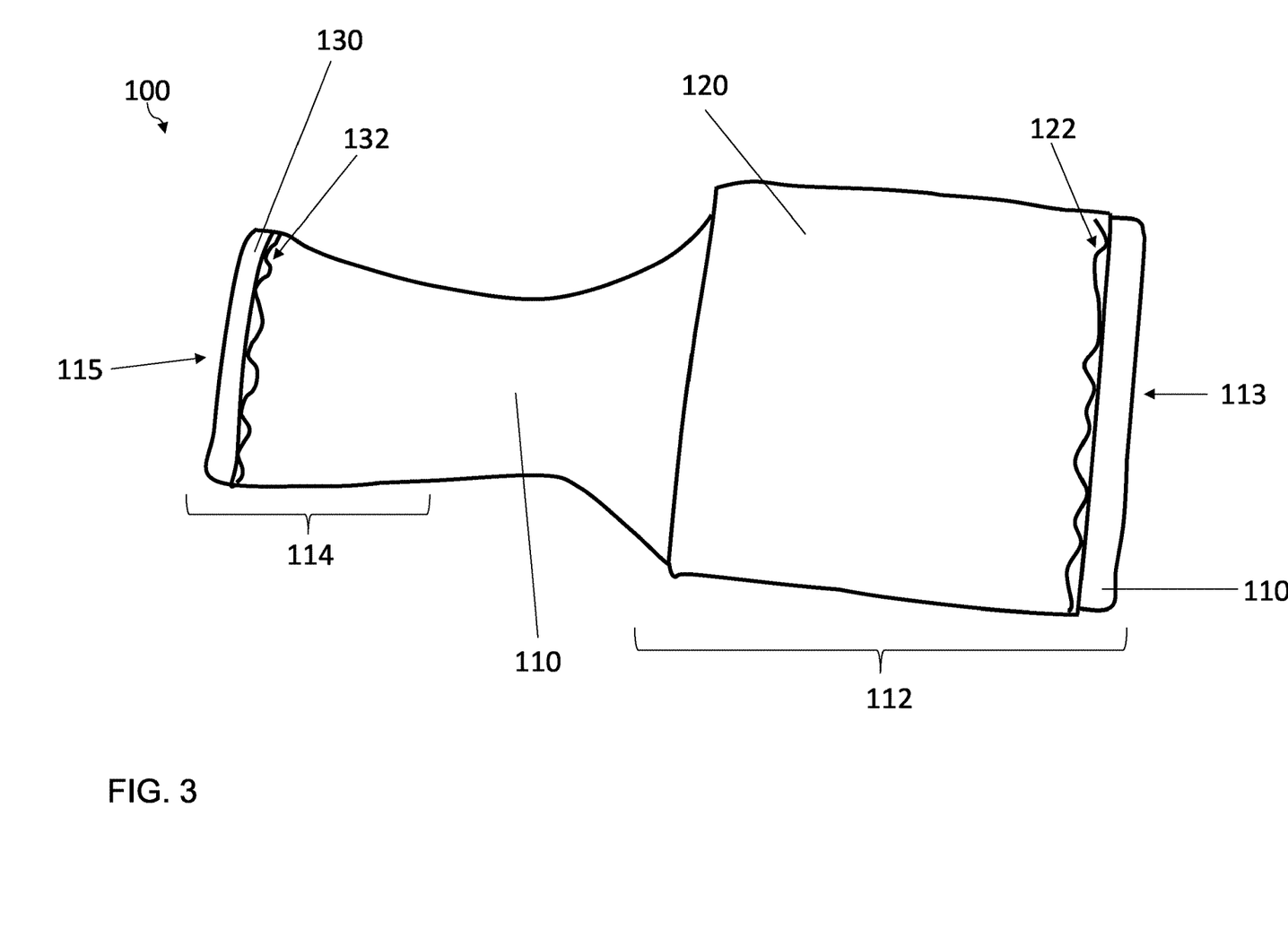
FIG. 3 is top view of a therapeutic sock according to an example implementation of the disclosed technology.

FIG. 3 illustrates an exemplary therapeutic sock 100 in accordance with some embodiments of the disclosed technology. The sock body 110 may be a stocking. The sock body 110 stretches around the foot of the user and adapts around the curvature of the user's foot. The sock body 110 may be elastic and may be made from a stretch fabric. The stretch fabric may be a 2-way or a 4-way stretch fabric. The stretch fabric may be made from nylon, neoprene, spandex, or elastane (e.g., Lycra™). The stretch fabric may be a combination of multiple types of fibers and may also include cotton, polyester, and/or wool. The sock body 110 may be breathable to allow airflow around the infected area. Additionally, the sock body 110's elastic nature is important to press the absorbent pad 120 against the user's foot. The material of sock body 110 must have a minimally adequate elasticity to keep the absorbent pad pressed with enough force against the toes to give the medicine sufficient pressure to absorb into the skin at the toes and/or foot. The elasticity of sock body 110 is also important to keep the absorbent pad in a specific place and only allow for minimal movement of the absorbent pad 120 underneath sock body 110. This keeps the medicine in one place on the toe and further allows it to absorb. For example, if the medicine is for the toenail, and the medicine is applied the absorbent pad above the toenail, the force of the sock body 110 presses the absorbent pad with the medicine onto the affected area of the toenail. This makes the medicine more effective over time by preventing the medicine from moving around to other locations, thereby becoming less concentrated on the affected area, which increases waste. The force pressing the sock body 110 against the toenail also ensures that the medicine is in firm contact with the affected area so that the medicine can help the affected area.

The lower section 112 of sock body 110 may contain absorbent pad 120 and toe end 113. Toe end 113 may be closed. At and/or near toe end 113, the absorbent pad 120 may be attached to sock body 110. Absorbent pad 120 may be attached to sock body 110 by a variety of means, such as sewing, gluing, binding, or plastic welding. The absorbent pad 120 may be of integral construction with sock body 110. The absorbent pad 120 may be sewn to sock body 110 with stitches 122. Stitches 112 can be of a variety of types including straight stitches, running stitches, baste stitches, back stitches, ladder stitches (e.g., invisible stitches), catch stitches, whip stitches, zig zag stitches or blanket stitches. Straight stitches may be advantageous to keep absorbent pad 110 attached to sock body 110. The thread used for the stitches may be a blend of cotton and polyester. The shape of the absorbent pad 120 may be square or rectangular. The absorbent pad 120 may have a length dimension (e.g., how far the absorbent pad extends over or under the toes) and a width dimension (e.g., over how many and/or which toes the absorbent pad 120 covers). The absorbent pad 120 may be sewn to the sock body 110 for entire width dimension of the absorbent pad 120 or only part of the width. The width of the absorbent pad 120 may be largely the same as the width of the sock body 110 at toe end 113 (when stretched).

The absorbent pad 120 may be arranged to extend between the top of the toes and foot and the top of sock body 110. Alternatively, the absorbent pad may be around to extend between the bottom of the toes and the foot and the sock bottom of sock body 110. The absorbent pad 120 may extend both above and below the toes and foot. By only extending the absorbent pad 120 above and below the toes and not on the sides of the toes or in between toes, the therapeutic sock 100 allows airflow to pass through between the toes and past the sides of the toes. This aids in treatment because the added airflow reduces the amount of sweat, which helps the medicine stay in one place and decreases the ability of common infections to spread and grow.

The absorbent pad 120 may be gauze. The gauze may be made from cotton, but may also include other materials as commonly known in the art. The gauze may be of a multiple-layer construction. The gauze may be 12-ply with 12 layers, but other types of gauze with different construction may be used. The gauze may be approximately 4 inches in length by approximately 4 inches in width, approximately 6 inches in length by approximately 6 inches in width, or approximately 8 inches in length by approximately 5 inches in width, but may be a variety of sizes for a variety of different ailments or treatment areas. The gauze may be sewn to sock body 110 with stitches 122 through all the layers. Alternately, the gauze may be sewn with stitches 122 only extending through some layers. The gauze may be parted so that one part extends over the top of the toes and foot and a second part extends under the bottom of the toes and foot. The absorbent pad 120 may be impregnated with medicine to heal toe and toenail ailments. The medicine may include an antibiotic, an antifungal, or an antiviral. The medicine may also include a moisturizer or moisturizing agent.

The upper section 114 of sock body 110 may contain restricting band 130 and ankle end 115. The ankle end 115 may surround the leg of the user directly above the ankle. To prevent the upper section 114 of sock body 110 from sliding down the user's leg and/or ankle, the upper section 114 may contain restricting band 130 at or near the ankle end 115. Restricting band 130 may be attached to sock body 110 by a variety of means, such as sewing, gluing, binding, or plastic welding. The restricting band 130 may be of integral construction with sock body 110. The restricting band 130 may be sewn to sock body 110 with stitches 122. Stitches 112 can be of a variety of types including straight stitches, running stitches, baste stitches, back stitches, ladder stitches (e.g., invisible stitches), catch stitches, whip stitches, zig zag stitches or blanket stitches. Zig zag stitches may be advantageous to keep restricting band 130 attached to sock body 110. 100 percent polyester thread may be used to attach restricting band 130 to sock body 110.

Restricting band 130 may be an elastic strap. Restricting band 130 may a nylon band or may be made from other similar materials exhibiting similar elastic properties, for example neoprene, spandex, or elastane (e.g., Lycra™). The restricting band 130 may have an unstretched length of about 6 to about 10 inches, about 7 to about 9 inches, or about 8 to 8.5 inches. The restricting band is also important for keeping the absorbent pad 110 in a specific place and only allow for minimal movement, which keeps the medicine on the absorbent pad 120 in the targeted treatment area. Additionally, because the absorbent pad 120 is between the sock body 110 and the user's foot and toes, the absorbent pad 120 may press against the sock body 110, causing it to stretch. The stretching of the sock body 110 may cause the sock body 110 to tend to slide down the user's leg and ankle and come off. The restricting band 130 prevents this from happening by gently constraining the ankle end 115 around the top of the user's foot. This prevents the therapeutic sock from sliding off the user's foot.

Figure 4:
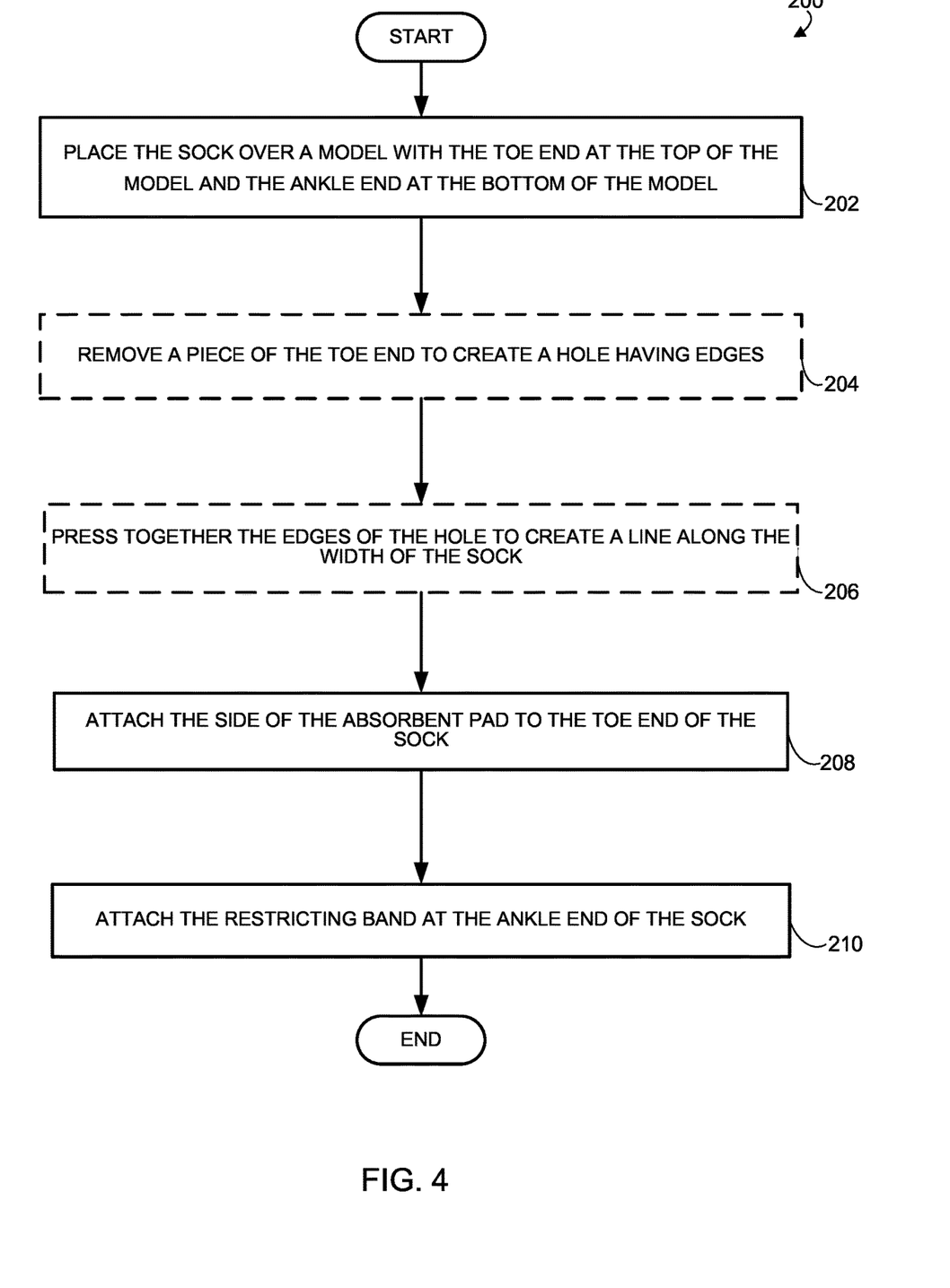
FIG. 4 is a flowchart of a method for constructing the therapeutic sock in accordance with certain embodiments of the disclosed technology.

FIG. 4 is a flow diagram illustrating an exemplary method 200 for manufacturing a therapeutic sock, in accordance with certain embodiments of the disclosed technology.

In block 202, the sock body 110 is placed over the foot model with the toe end 113 at the top of the model and the ankle end 115 at the bottom of the model. The foot model may be a mannequin or a tailor's model of a similar nature. The sock body 110 should be placed on the foot model inside-out. The sock body 110 should be positioned so that the material is stretched.

In optional block 204, a piece of the sock at the toe end is removed with a cutting device, such as scissors. Removing the end of a sock may create a hole. The hole may have edges in a circular or ovular shape.

In optional block 206, the edges of the hole may be pressed together to create a line. The line may have a length that is equal in width to the absorbent pad 120. The line may be the end of the two sides of sock body 110.

In block 208, the absorbent pad 120 may be attached to the toe end 113 of the therapeutic sock. Absorbent pad 120 may be attached to sock body 110 by a variety of means, such as sewing, gluing, binding, or plastic welding. The absorbent pad 120 may be sewn to sock body 110 with stitches 122. Stitches 112 can be of a variety of types including straight stitches, running stitches, baste stitches, back stitches, ladder stitches (e.g., invisible stitches), catch stitches, whip stitches, zig zag stitches, or blanket stitches. The absorbent pad 120 may be sewn directly to the area immediately adjacent to the line created from the edges of the hole in optional block 206. This allows the stitch to go through the absorbent pad 120, and both sides of sock body 110.

In block 210, the restricting band 210 may be attached to the ankle end 114 of the therapeutic sock. Restricting band 130 may be attached to sock body 110 by a variety of means, such as sewing, gluing, binding, or plastic welding. The restricting band 130 may be sewn to sock body 110 with stitches 122. Stitches 112 can be of a variety of types including straight stitches, running stitches, baste stitches, back stitches, ladder stitches (e.g., invisible stitches), catch stitches, whip stitches, zig zag stitches or blanket stitches.

After block 210, the completed therapeutic sock may have medication applied to the absorbent pad 120.

As an alternative to method 200, the therapeutic sock may be constructed from a custom-made sock body 110 with an open toe end 113. If that was the case, then removing the toe end 113 would not be required. Additionally, sock body 110 could be constructed with a flap or fold for containing restricting band 130. This would allow the restricting band 130 to be located in the flap and provide the force necessary to secure the therapeutic sock on the ankle of the user with minimal sewing necessary.

The completed therapeutic sock may be removed from the foot model and may be left inside-out. The therapeutic sock may be delivered to the user inside-out. That way the user can apply medication to the absorbent pad 120 when it is easily accessible. Once the medication has been applied to the absorbent pad 120, the user may position the absorbent pad 120 appropriately on the infected area of the foot. While holding the absorbent pad 120 in the appropriate location, the user may then expand the restricting band 130 to and pull the restricting band 130 around the foot and up to the ankle. The absorbent pad 120 will then remain in place as held by the sock body 110 and restrictive band 130. The user can then move around as desired while keeping the medicine positioned appropriately on the toes. The nylon sock body 110 furthermore is lightweight, breathable, and can be worn inside a shoe.

In some examples, disclosed systems or methods may involve one or more of the following clauses:

Clause 1: A therapeutic sock comprising: an upper section configured to extend up a leg of a user, the upper section comprising a restricting band configured to restrict a first width of the upper section thereby holding the therapeutic sock in place; a lower section configured to surround toes of the user, the lower section comprising a front portion, a first side, a second side opposite the first side, a second width extending from the first side to the second side that is greater than the first width, and a first length extending from the front portion to the upper section; and a gauze pad attached to the front portion of the lower section along the second width.

Clause 2: The therapeutic sock of clause 1, wherein the therapeutic sock is constructed from a 4-way stretch fabric.

Clause 3: The therapeutic sock of clause 2, wherein the 4-way stretch fabric is nylon.

Clause 4: The therapeutic sock of clause 1, wherein the restricting band comprises an elastic strap.

Clause 5: The therapeutic sock of clause 4, wherein the elastic strap comprises a nylon band measuring from about 6 to about 10 inches in unstretched length.

Clause 6: The therapeutic sock of clause 4, wherein the elastic strap is sown to the upper section using zig zag stitches.

Clause 7: The therapeutic sock of clause 1, wherein the gauze pad comprises medicine configured to be delivered to a top of a foot of the user, a bottom of a foot of the user or combinations thereof.

Clause 8: The therapeutic sock of clause 7, wherein the medicine comprises an antibiotic, an antifungal, an antiviral, a moisturizer, or combinations thereof.

Clause 9: The therapeutic sock of clause 1, wherein the gauze pad is sown to the lower section using straight stitches.

Clause 10: A therapeutic stocking comprising: an upper section configured to extend up a leg of a user, the upper section comprising a restricting band configured to restrict a first width of the upper section thereby holding the therapeutic stocking in place; a lower section for configured to surround toes of the user, the lower section comprising a front portion, a first side, a second side opposite the first side, a second width extending from the first side to the second side that is greater than the first width, and a first length extending from the front portion to the upper section; and an absorbent pad attached to the front portion of the lower section along the second width.

Clause 11: The therapeutic stocking of clause 10, wherein the absorbent pad is gauze, and the lower section and the upper section are constructed of nylon.

Clause 12: The therapeutic stocking of clause 11, wherein the gauze contains medicine configured to be delivered to tops of the toes, and the medicine is an antibiotic, an antifungal, an antiviral, a moisturizer, or combinations thereof.

Clause 13: The therapeutic stocking of clause 10, wherein the absorbent pad is attached to the first width of the lower section by straight stitches.

Clause 14: The therapeutic stocking of clause 10, wherein the restricting band comprises an elastic strap measuring about 6 inches to about 10 inches in unstretched length.

Clause 15: A sock comprising: an upper section configured to extend around an ankle of a user, the upper section comprising a restricting band; a lower section configured to surround toes of the user, the lower section comprising a front portion, a first side, a second side opposite the first side, a width extending from the first side to the second side; and an absorbent pad attached to the front portion of the lower section along the width.

Clause 16: The sock of clause 15, wherein the absorbent pad is gauze, and the lower section and the upper section are constructed of nylon.

Clause 17: The sock of clause 15, wherein the restricting band prevents the sock from sliding off the ankle and comprises an elastic strap.

Clause 18: The sock of clause 15, wherein the absorbent pad comprises medicine configured to be delivered to a top of toes of the user.

Clause 19: The sock of clause 18, wherein the medicine comprises an antibiotic, an antifungal, an antiviral, a moisturizer, or combinations thereof.

Clause 20: The sock of clause 15, wherein the absorbent pad is attached to the width of the lower section by straight stitches.

Certain embodiments and implementations of the disclosed technology are described above with reference to block and flow diagrams of systems and methods. Likewise, some blocks of the block diagrams and flow diagrams may not necessarily need to be performed in the order presented, may be repeated, or may not necessarily need to be performed at all, according to some embodiments or implementations of the disclosed technology.

In this description, numerous specific details have been set forth. It is to be understood, however, that implementations of the disclosed technology may be practiced without these specific details. In other instances, well-known methods, structures, and techniques have not been shown in detail in order not to obscure an understanding of this description. References to "one embodiment," "an embodiment," "some embodiments," "example embodiment," "various embodiments," "one implementation," "an implementation," "example implementation," "various implementations," "some implementations," etc., indicate that the implementation(s) of the disclosed technology so described may include a particular feature, structure, or characteristic, but not every implementation necessarily includes the particular feature, structure, or characteristic. Further, repeated use of the phrase "in one implementation" does not necessarily refer to the same implementation, although it may.

Throughout the specification and the claims, the following terms take at least the meanings explicitly associated herein, unless the context clearly dictates otherwise. The term "connected" means that one function, feature, structure, or characteristic is directly joined to or in communication with another function, feature, structure, or characteristic. The term "coupled" means that one function, feature, structure, or characteristic is directly or indirectly joined to or in communication with another function, feature, structure, or characteristic. The term "or" is intended to mean an inclusive "or." Further, the terms "a," "an," and "the" are intended to mean one or more unless specified otherwise or clear from the context to be directed to a singular form. By "comprising" or "containing" or "including" is meant that at least the named element, or method step is present in article or method, but does not exclude the presence of other elements or method steps, even if the other such elements or method steps have the same function as what is named.

It is to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

Although embodiments are described herein with respect to systems or methods, it is contemplated that embodiments with identical or substantially similar features may alternatively be implemented as systems, and/or methods.

As used herein, unless otherwise specified, the use of the ordinal adjectives "first," "second," "third," etc., to describe a common object, merely indicates that different instances of like objects are being referred to, and is not intended to imply that the objects so described must be in a given sequence, either temporally, spatially, in ranking, or in any other manner.

While certain embodiments of this disclosure have been described in connection with what is presently considered to be the most practical and various embodiments, it is to be understood that this disclosure is not to be limited to the disclosed embodiments, but on the contrary, is intended to cover various modifications and equivalent arrangements included within the scope of the appended claims. Although specific terms are employed herein, they are used in a generic and descriptive sense only and not for purposes of limitation.

This written description uses examples to disclose certain embodiments of the technology and also to enable any person skilled in the art to practice certain embodiments of this technology, including making and using any apparatuses or systems and performing any incorporated methods. The patentable scope of certain embodiments of the technology is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A therapeutic sock comprising:
   an upper section configured to extend up a leg of a user, the upper section comprising a restricting band configured to restrict a first width of the upper section thereby holding the therapeutic sock in place, wherein the restricting band comprises an elastic strap sewn to the upper section using zig zag stitches;

a lower section configured to surround toes of the user, the lower section comprising a front end having a second width, a first side, a second side opposite the first side, the second width extending from the first side to the second side that is greater than the first width, and a first length extending from the front end to the upper section; and a gauze pad attached to the front end of the lower section along the second width, wherein:
the gauze pad is sewn to the lower section using straight stitches,
the gauze pad comprises multiple layers separated to create a first portion and a second portion,
the first portion is configured to extend over the toes of the user,
the second portion is configured to extend under the toes of the user,
the gauze pad does not extend in between the toes, thereby improving airflow around the toes, and
the gauze pad comprises medicine selected from a group consisting of an antibiotic, an antifungal, an antiviral, a moisturizer, or combinations thereof, and
wherein the therapeutic sock comprises a stretch fabric configured to press the gauze pad against the toes.

2. The therapeutic sock of claim 1, wherein the stretch fabric is a 4-way stretch fabric.

3. The therapeutic sock of claim 2, wherein the 4-way stretch fabric is nylon.

4. The therapeutic sock of claim 1, wherein the elastic strap comprises a nylon band measuring from about 6 to about 10 inches in unstretched length.

5. The therapeutic sock of claim 1, wherein:
the gauze pad is 12 ply and comprises 12 layers, and
the gauze pad is approximately 4 inches in length by approximately 4 inches in width.

6. The therapeutic sock of claim 1, wherein the therapeutic sock is configured to be delivered to a user in an inside-out configuration to enable the user to apply a medicine to the gauze pad and position the gauze pad on the infected area of the foot.

7. The therapeutic sock of claim 1, wherein the upper section comprises a flap for holding the restricting band.

8. The therapeutic sock of claim 1, wherein the therapeutic sock is disposable.

9. A therapeutic stocking comprising:
an upper section configured to extend up a leg of a user, the upper section comprising a restricting band configured to restrict a first width of the upper section thereby holding the therapeutic stocking in place, wherein the restricting band comprises an elastic strap sewn to the upper section using zig zag stitches;
a lower section for configured to surround toes of the user, the lower section comprising a front end having a second width, a first side, a second side opposite the first side, the second width extending from the first side to the second side that is greater than the first width, and a first length extending from the front end to the upper section; and
an absorbent pad attached to the front end of the lower section along the second width, wherein:
the absorbent pad is sewn to the lower section using straight stitches,
the absorbent pad comprises multiple layers separated to create a first portion and a second portion,
the first portion is configured to extend over the toes of the user,
the second portion is configured to extend under the toes of the user,
the absorbent pad does not extend in between the toes, thereby improving airflow around the toes, and
the absorbent pad comprises medicine selected from a group consisting of an antibiotic, an antifungal, an antiviral, a moisturizer, or combinations thereof, and
wherein the therapeutic stocking comprises a stretch fabric configured to press the absorbent pad against the toes.

10. The therapeutic stocking of claim 9, wherein the absorbent pad is gauze, and the lower section and the upper section are constructed of nylon.

11. The therapeutic stocking of claim 9, wherein the restricting band comprises an elastic strap measuring about 6 inches to about 10 inches in unstretched length.

12. A sock comprising:
an upper section configured to extend around an ankle of a user, the upper section comprising a restricting band, wherein the restricting band comprises an elastic strap sewn to the upper section using zig zag stitches;
a lower section configured to surround toes of the user, the lower section comprising a front end having a width, a first side, a second side opposite the first side, the width extending from the first side to the second side; and
an absorbent pad attached to the front end of the lower section along the width, wherein:
the absorbent pad is sewn to the lower section using straight stitches,
the absorbent pad comprises multiple layers separated to create a first portion and a second portion,
the first portion is configured to extend over the toes of the user,
the second portion is configured to extend under the toes of the user,
the absorbent pad does not extend in between the toes, thereby improving airflow around the toes, and
the absorbent pad comprises medicine selected from a group consisting of an antibiotic, an antifungal, an antiviral, a moisturizer, or combinations thereof, and
wherein the sock comprises a stretch fabric configured to press the absorbent pad against the toes.

13. The sock of claim 12, wherein the absorbent pad is gauze, and the lower section and the upper section are constructed of nylon.

* * * * *